United States Patent
Hall et al.

(10) Patent No.: US 8,171,591 B2
(45) Date of Patent: May 8, 2012

(54) POWER TOOTHBRUSH BRUSHHEAD WITH FLUID-DIRECTING MEMBER

(75) Inventors: Scott E. Hall, Issaquah, WA (US); Kevin A. Miller, Bellevue, WA (US); Joseph W. Grez, North Bend, WA (US); Ronald C. Lilley, Federal Way, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 812 days.

(21) Appl. No.: 10/581,221

(22) PCT Filed: Dec. 9, 2004

(86) PCT No.: PCT/IB2004/052821
§ 371 (c)(1),
(2), (4) Date: Oct. 3, 2007

(87) PCT Pub. No.: WO2005/055863
PCT Pub. Date: Jun. 23, 2005

(65) Prior Publication Data
US 2008/0028548 A1 Feb. 7, 2008

Related U.S. Application Data

(60) Provisional application No. 60/528,628, filed on Dec. 11, 2003.

(51) Int. Cl.
*A46B 13/00* (2006.01)
(52) U.S. Cl. .......................................... 15/22.2; 15/22.1
(58) Field of Classification Search ............... 15/22.1, 15/28, 110, 22.2
See application file for complete search history.

(56) References Cited

U.S. PATENT DOCUMENTS

| | | | | |
|---|---|---|---|---|
| 1,588,785 A * | 6/1926 | Van Sant | | 15/110 |
| 2,117,174 A * | 5/1938 | Jones | | 15/110 |
| 2,312,828 A | 3/1943 | Adamsson | | |
| 2,545,814 A * | 3/1951 | Kempster | | 15/188 |
| 2,702,914 A * | 3/1955 | Kittle et al. | | 15/114 |
| 3,181,189 A | 5/1965 | Leyden | | |
| 3,316,576 A * | 5/1967 | Urbush | | 15/22.1 |
| 4,277,862 A * | 7/1981 | Weideman | | 15/110 |
| 4,458,374 A * | 7/1984 | Hukuba | | 15/22.1 |
| 5,604,951 A * | 2/1997 | Shipp | | 15/167.1 |
| 5,689,850 A * | 11/1997 | Shekalim | | 15/22.1 |
| 5,735,011 A * | 4/1998 | Asher | | 15/167.1 |
| 6,041,467 A * | 3/2000 | Roberts et al. | | 15/167.1 |
| 6,513,182 B1 * | 2/2003 | Calabrese et al. | | 15/110 |
| 6,859,969 B2 * | 3/2005 | Gavney et al. | | 15/117 |
| 7,181,799 B2 * | 2/2007 | Gavney et al. | | 15/22.1 |

(Continued)

FOREIGN PATENT DOCUMENTS

GB 2371217 A 7/2002

*Primary Examiner* — Randall Chin

(57) ABSTRACT

The brushhead includes a brushhead member which includes a bristle field, the brushhead member being adapted for cleaning teeth as part of a power toothbrush, wherein the brushhead in operation moves in a reciprocating action. In one embodiment the brushhead includes a rim member which extends around at least a substantial portion of the brushhead, the rim member extending around the entire bristle field and having an upper edge which is lower than the top of the bristles. The rim member has a different flexibility than the bristles so that the movement of the rim member and the bristles is out of phase during operation of the toothbrush, which results in fluid from the bristles being directed toward the teeth during operation of the toothbrush.

12 Claims, 4 Drawing Sheets

U.S. PATENT DOCUMENTS

| | | |
|---|---|---|
| 2002/0124337 A1 | 9/2002 | Calabrese et al. |
| 2003/0033680 A1 | 2/2003 | Davies et al. |
| 2003/0077107 A1 | 4/2003 | Kuo |
| 2003/0196283 A1 * | 10/2003 | Eliav et al. .................... 15/22.1 |

* cited by examiner

POWER TOOTHBRUSH BRUSHHEAD WITH FLUID-DIRECTING MEMBER

CROSS REFERENCE TO RELATED APPLICATION

This application claims the benefit of U.S. provisional application Ser. No. 60/528,628 filed Dec. 11, 2003, which is incorporated herein whole by reference.

TECHNICAL FIELD

This invention relates generally to brushheads for power toothbrushes, and more specifically concerns such brushheads which include elements which operate in combination with the brushhead bristles to improve the direction of fluid flow toward the teeth and gums of the user.

BACKGROUND OF THE INVENTION

In most power toothbrushes, it is desirable that the reciprocating action of the bristles direct as much fluid as possible toward the teeth and gums of the user, in order to promote desired clinical effects, including cleaning, as well as a desirable sensory effect on the teeth and gums for the user. Certain types of reciprocal brushhead motion, including for instance rotary-type motion, may in some cases produce a splayed fluid action, resulting in a reduced clinical effect and sensory effect relative to other types of reciprocating brushhead action. It is desirable to have as much fluid as possible from the action of the bristles be directed toward the teeth and gums of the user providing cleaning and a sensory effect for the user.

SUMMARY OF THE INVENTION

Accordingly, one aspect of the present invention is a rimmed brushhead for a power toothbrush, comprising: a brushhead member which includes a bristle field, adapted for cleaning teeth as part of a power toothbrush, wherein the brushhead member in operation moves in a reciprocating action; and a rim member extending around at least a substantial portion of the bristle field of the brushhead, the rim member having an upper edge which is lower than the top of the bristles, and otherwise configured and arranged to produce action of fluid moving off of the bristles toward the teeth during operation of the toothbrush Another aspect of the present invention is a brushhead for a power toothbrush, comprising: a brushhead member which includes a bristle field, adapted for cleaning teeth as part of a power toothbrush, wherein the brushhead member in operation moves in a reciprocating action; and at least one paddle member positioned on the brushhead member, the bristle field extending around a substantial portion of the paddle member, the paddle member extending upwardly from a bristle base with the bristles, wherein the paddle member is not as high as the bristle field, and otherwise configured and arranged to produce action of fluid moving off of the bristles toward the teeth during operation of the toothbrush.

BEST MODE FOR CARRYING OUT THE INVENTION

Figure 1:
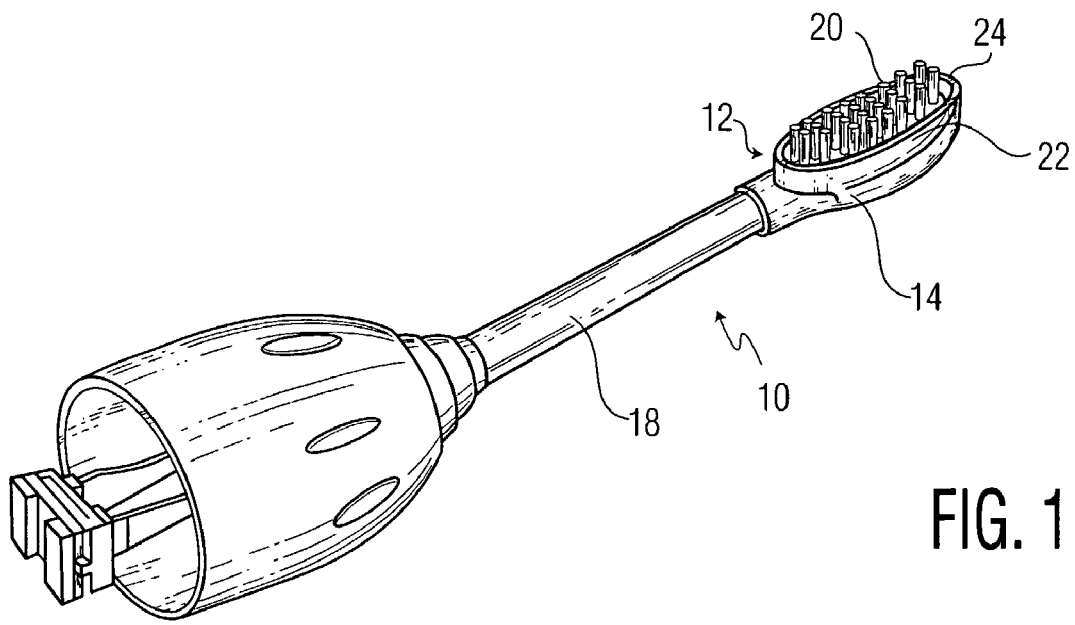
FIG. 1 is a perspective view showing both a power toothbrush brushhead and a rim structure of the present invention adapted to fit on the brushhead.
Figure 2:
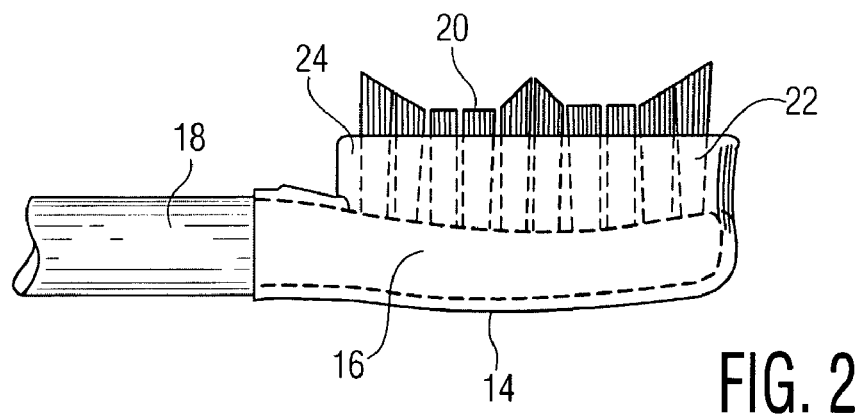
FIG. 2 is a side elevational view showing the rim structure in place on the brushhead.
Figure 3:
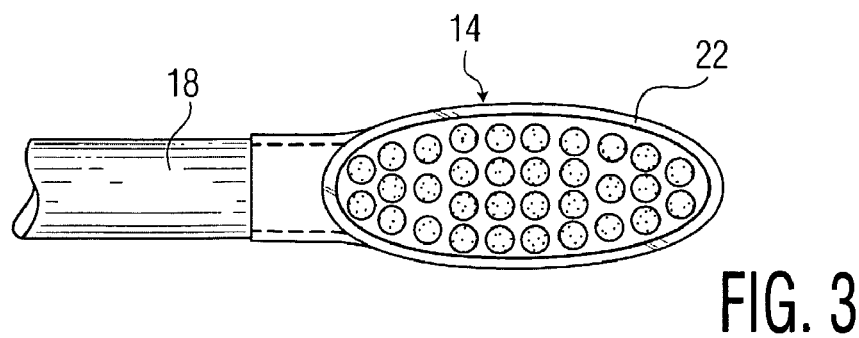
FIG. 3 is a front view showing the rim structure in place on the brushhead.

FIGS. 1-3 show a first embodiment of a fluid-directing brushhead assembly of the present invention, referred to generally at 10. Brushhead assembly 10 includes a brushhead 12 for a power toothbrush and a rim structure 14. Brushhead 12 is a conventional member comprising a base portion 16 which extends from a stem or arm member portion 18 of a toothbrush and a plurality of tufts of toothbrush bristles arranged in a selected configuration, referred to herein as a bristle field 20. The elements of brushhead 12 are conventional and thus can vary in structure and arrangement within the spirit of the present invention.

In one embodiment, the rim structure 14 fits over and around base portion 16, like a glove or boot, extending a small distance back along the stem/arm portion 18, approximately ¼ inch in the embodiment shown, although this can be varied. The rim structure is bonded to the rear surface of brushhead 12. Rim structure 14 includes a fluid rim portion 22, encircling the bristle field 20 to a height which in the embodiment shown is approximately one-half of the height of the highest bristles in the bristle field. The height of the fluid rim portion 22 can vary to some extent, but should be less than the height of the lowest bristles in the bristle field so that it will not touch the teeth, yet high enough to provide a fluid directing effect, as discussed below. If the rim portion is too short relative to the height of the bristles, the rim structure will not provide the desired fluid directing and pumping effects.

Typically, the upper edge 24 of the fluid rim portion 22 will be flat around its periphery. In the embodiment shown, fluid rim portion 22 is continuous and without any openings, although in some cases it can include open areas at points along its length. Generally, the open areas will be at a minimum, since the purpose of fluid rim portion 22 is to direct fluid moving off the bristles outwardly toward the teeth.

The rim structure material typically and preferably is a flexible elastomeric material, although the material need not necessarily be flexible. Typically, the flexibility of the fluid rim portion 22 will be different than the flexibility of the bristles/bristle tufts, to produce the "pumping" action for the fluid off the bristles toward the teeth/gums. Fluid rim portion 22 forms a boundary for bristle movement, since the bristles will come into contact with the rim portion as they move back and forth, and acts as a deflector/guide to direct fluid directly toward the teeth and gums. The angle of fluid direction (angle of attack) toward the teeth will be generally approximately 90°±.

In operation, the movement of the bristles in the bristle field 20 will be out of phase with the movement of the fluid rim portion 22, which also generally moves in response to movement of the brushhead, due to differences in flexibility between the fluid rim portion and the bristle tufts, resulting in a "pumping" effect for the fluid. This pumping effect produces a fluid movement toward the teeth and gums of the user.

Fluid which comes off of the bristles during operation without a rim structure, particularly the fluid directed to the sides of the brushhead, is now substantially all directed toward the teeth with the present invention, resulting in possible improved clinical effects as well as improved sensory effect relative for the user.

Although the rim structure 14 as shown in the embodiment of FIGS. 1-3 is a separate element, which is inserted over the brushhead, the rim structure 14, including specifically the rim portion 22 thereof, can be made integral with the brushhead; the configuration of the rim portion, however, will remain the same as shown for the separate element and will function substantially identical thereto.

Figure 4:
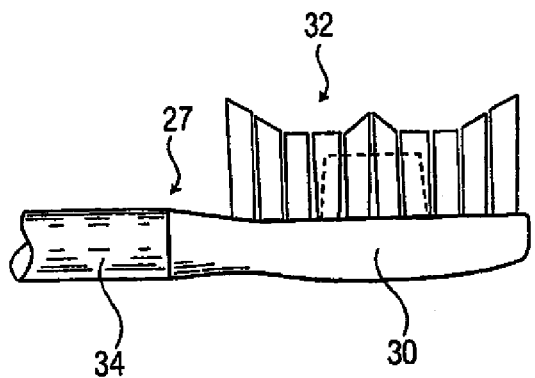
FIG. 4 is side elevational view of an alternative embodiment to the embodiment of FIGS. 1-3.
Figure 5:
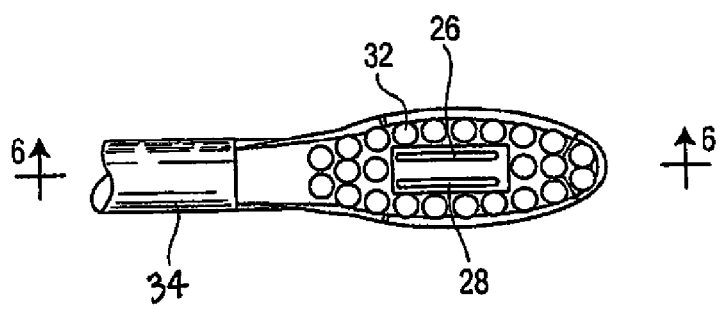
FIG. 5 is a front view of the embodiment of FIG. 4.
Figure 6:
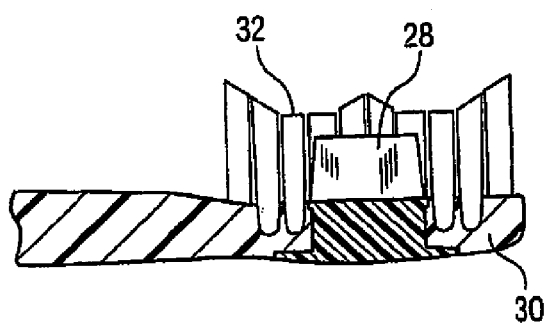
FIG. 6 is a cross-sectional view of the embodiment of FIGS. 4-5.
Figure 7:
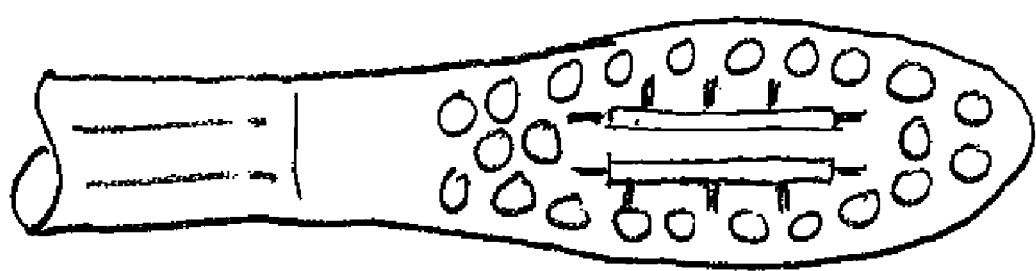
FIG. 7 is a top view showing an embodiment with wing portions.
Figure 8:
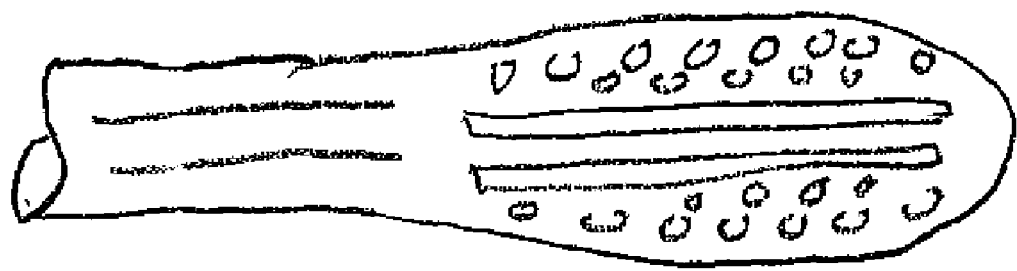
FIG. 8 is a top view of a variation of the embodiment of FIG. 4.

FIGS. 4, 5 and 6 show another embodiment of the fluid-directing brushhead of the present invention. The brushhead 27 of this embodiment also includes a brushhead base 30 extending from a stem/arm member 34, and a plurality of bristle tufts extending upwardly therefrom, defining a bristle field 32. In this embodiment, the fluid-directing member includes two paddle-like elements 26, 28 which are located centrally of brushhead 27, encircled by bristle field 32. In the embodiment shown, paddle elements 26, 28 extend longitudinally of the brushhead and are approximately 0.35 inches long, 0.28 inches high and approximately 0.03 inches thick and are made from a flexible material, such as an elastomer or similar material.

Paddle elements 26, 28 could, however, extend for substantially the entire length of the brushhead thus dividing the bristle field in two, longitudinally. Also, the paddle elements 26, 28 are both shorter than the shortest bristle; in the embodiment shown, they are approximately 0.25 inches shorter than the tallest bristles, and approximately 0.08 inches shorter than the shortest bristles. However, it should be understood that the dimensions of the paddle elements can vary. It is important, however, that the paddle elements be shorter than the shortest bristles.

While in the embodiment shown, paddles 26 and 28 are substantially identical, they could differ in configuration or materials so that their movement will be out of phase to some degree with each other. The paddles could also be out of phase with the bristles.

Pumping action results from differential motion between the two paddles, as well as differential motion between the paddles and the bristle tufts. While the paddle elements are generally flexible, they could be stiff or substantially stiff as well. Typically, the paddles will be stiffer than the bristles. In some cases, the height of the paddle elements can be close enough to the height of the bristles but still less than the height of the bristles to create a shear-type cleaning effect for the teeth of a user.

Although the embodiment shown includes two parallel paddle elements, a single paddle element will also provide desired results. In a modified configuration, the paddles could be non-parallel, although they will still be generally oriented longitudinally of the brushhead. Further, a single paddle could be used with wings extending therefrom at points along the length of the paddle.

In operation of this embodiment, similar to the rim structure embodiment, the differential motion between the bristles and the paddle elements and/or the two paddle elements creates a "pumping" effect for the fluid outwardly from the brushhead, most of the fluid being at 90° to the brushhead, in the direction of the teeth and gums. The movement of the fluid produced by action of the disclosed brushhead will thus be more controlled in the direction of the teeth and gums than with a conventional brushhead and more effective, clinically and in a sensory manner as well.

Accordingly, toothbrush brushhead arrangements have been disclosed which assist in directing fluid away from the brushhead in the direction of the teeth and gums. This can result in improved cleaning, but also an improvement in the sensory experience of the user.

Although a preferred embodiment of the invention has been disclosed for purposes of illustration, it should be understood that various changes, modifications and substitutions may be incorporated in the embodiment without departing from the spirit of the invention which is defined by the claims which follow.

What is claimed is:

1. A rimmed powered brushhead which operates as part of a power toothbrush, comprising:
    a powered brushhead member, which includes a bristle field having lowest bristles and tallest bristles in a base portion, adapted for cleaning teeth as part of a power toothbrush, wherein the brushhead member in operation moves by power in a reciprocating action; and
    a rim member extending around at least a substantial portion of the bristle field of the brushhead, the rim member having a flat upper edge which is positioned lower than the top of the lowest bristles and higher than one-half the height of the tallest bristles in the bristle field above an upper surface of the base portion, and otherwise configured and arranged to produce movement of fluid from the bristles toward the teeth during operation of the toothbrush.

2. The brushhead of claim 1, wherein the rim member is substantially continuous around the bristle field.

3. The brushhead of claim 1, wherein there is a difference in flexibility between the rim member and the bristles in the bristle field, resulting in differential motion between the bristles and the rim member and a pumping action for the fluid toward the teeth.

4. The brushhead of claim 1, wherein the rim member is separate from the brushhead member.

5. The brushhead of claim 1, wherein the rim member is integral with the brushhead member.

6. The brushhead of claim 1, wherein substantially all of the fluid moving off the bristles is directed toward the teeth and gums of a user.

7. A powered brushhead adapted for a power toothbrush, comprising:
    a powered brushhead member, which includes a bristle field, adapted for cleaning teeth as part of a power toothbrush, wherein the brushhead member in operation moves by power in a reciprocating action;
    at least two paddle members positioned on the brushhead member, the paddle members each being straight, continuous, substantially equal in size, and extending substantially longitudinally of the brushhead, parallel with a neck portion of the brushhead member, such that the bristle field extends entirely around the paddle members, the paddle members extending upwardly from a bristle base with the bristles, wherein the paddle members are not as high as the bristle field, so that a shear-type fluid cleaning effect on the teeth is produced, wherein there are no bristles between the two paddle members, wherein the paddle members are structurally characterized in configuration and arrangement relative to the bristle field to produce movement of fluid from the bristles toward the teeth rather than contacting the teeth during operation of the toothbrush.

8. The brushhead of claim 7, wherein the paddle members are parallel.

9. The brushhead of claim 7, wherein the paddle members are sufficiently different in configuration or material that they move out of phase with each other during movement of the brushhead.

10. The brushhead of claim 7, wherein the paddle members have a different flexibility from the bristles.

11. The brushhead of claim 7, including wing portions which extend outwardly from the paddle along the length thereof.

12. The brushhead of claim 7, including wing portions at opposing ends of the paddle members.

\* \* \* \* \*